(12) United States Patent
Zhou et al.

(10) Patent No.: US 6,578,409 B1
(45) Date of Patent: Jun. 17, 2003

(54) METHOD AND DEVICE FOR DETERMINING THE THRESHOLD OF HEAVY FRACTION DEPOSIT CONTAINED IN A LIQUID HYDROCARBON FLUID

(75) Inventors: Honggang Zhou, Pau (FR); Jacques Jose, Villette de Vienne (FR); Daniel Broseta, Paris (FR); Michel Robin, Poissy (FR); Marc Durandeau, Saint-Nom-la-Bretèche (FR)

(73) Assignee: Institut Francais du Petrole, Rueil-Malmaison cedex (FR)

( * ) Notice: Subject to any disclaimer, the term of this patent is extended or adjusted under 35 U.S.C. 154(b) by 0 days.

(21) Appl. No.: 09/869,204

(22) PCT Filed: Nov. 8, 2000

(86) PCT No.: PCT/FR00/03099
§ 371 (c)(1),
(2), (4) Date: Feb. 6, 2002

(87) PCT Pub. No.: WO01/35067
PCT Pub. Date: May 17, 2001

(30) Foreign Application Priority Data

Nov. 9, 1999 (FR) ............................................ 99 14060

(51) Int. Cl.[7] ............................................... G01N 33/28
(52) U.S. Cl. .................... 73/53.01; 73/54.09; 73/61.41; 73/64.56; 73/864.72; 73/864.87
(58) Field of Search .......................... 73/53.01, 61.41, 73/64.56, 54.04, 54.09, 54.11, 864.71, 864.72, 864.87

(56) References Cited

U.S. PATENT DOCUMENTS

| | | | |
|---|---|---|---|
| 3,512,940 A | * | 5/1970 | Shapiro ..................... 73/61.41 |
| 4,403,502 A | * | 9/1983 | Lindt ......................... 73/54.09 |
| 4,455,860 A | | 6/1984 | Cullick et al. |

FOREIGN PATENT DOCUMENTS

| | | |
|---|---|---|
| EP | 0313972 | 5/1989 |
| EP | 0473472 | 3/1992 |
| WO | 9610745 | 4/1996 |

* cited by examiner

Primary Examiner—Daniel S. Larkin
(74) Attorney, Agent, or Firm—Antonelli, Terry, Stout & Kraus, LLP

(57) ABSTRACT

The invention concerns a method whereby a fluid sample is brought (1) at constant pressure Pe and temperature maintaining the heavy fractions, in particular asphaltenes, in dissolved state and/or in stable colloidal state, at the intake (4) of a capillary passage with high pressure drop. Said sample is forced to flow through the capillary conduit, at an increasing flow rate. The method consists in measuring (11) the fluid pressure Ps and the fluid flow rate D (12) at the outlet (5) of the capillary conduit and in representing the variation curve of the quantity $\Delta P = Pe - Ps$ or the quantity D as a function of the other quantity or as a function of time. The deposit pressure, characteristic of the threshold of deposit of heavy fractions, is defined as the value of pressure Ps, which corresponds to a change of the slope in the variation curve of the quantity $\Delta P$ or the quantity D.

23 Claims, 4 Drawing Sheets

METHOD AND DEVICE FOR DETERMINING THE THRESHOLD OF HEAVY FRACTION DEPOSIT CONTAINED IN A LIQUID HYDROCARBON FLUID

FIELD OF THE INVENTION

The invention concerns a method for determining the threshold of deposition of heavy fractions, i.e., according to the invention, generally asphaltenic polar fractions, that are contained in the dissolved and/or stable colloidal state in a liquid hydrocarbon-containing fluid. It further concerns a device for implementing said method.

Many petroleum crudes, notably those referred to as asphaltenic petroleum crudes, are liquid hydrocarbon-containing fluids that contain more or less large quantities of heavy fractions in the dissolved and/or stable colloidal state under the pressure and temperature conditions which said fluids are subjected to. When these pressure and/or temperature conditions vary, notably when the pressure decreases, the heavy fractions contained in these fluids tend to flocculate and to settle in the formation surrounding the wells, in the wells and in the production and transfer facilities intended for said fluids. Thus, when a hydrocarbon reservoir containing heavy fractions is developed, the stability of these fractions decreases generally before the bubble point is reached. When the saturation threshold is reached, the heavy fractions flocculate and settle, which can lead to clogging of the porous media and formation of plugs likely to cause severe damage to the production wells and to the surface installations.

For petroleum producers, who have to extract and to convey, through production wells and pipe networks, liquid hydrocarbon-containing fluids consisting of petroleum crudes containing heavy fractions, for example asphaltenic petroleum crudes, coming from production fields, it is therefore important to precisely know the pressure thresholds above which heavy fractions settle, so as to carry out production and transfer of said fluids under pressure and temperature conditions that prevent heavy fraction deposition in the facilities, or to provide a suitable treatment.

BACKGROUND OF THE INVENTION

There are various known methods for determining the deposition threshold of heavy fractions, notably asphaltenes, contained in liquid hydrocarbon-containing fluids consisting of petroleum crudes. These methods are most often optical light transmission or scattering methods, conductimetric methods, or viscometric methods.

The aforementioned methods involve detection of the variation of a physical quantity, for example the absorption coefficient or absorbance of light beams in the visible range or in the infrared, the electrical conductivity, or the viscosity, which is due to a change in the consistency of the fluid as a result of the flocculation and the deposition of the heavy fractions.

A major drawback of such methods is that they are not very selective insofar as the variation of the physical quantity measured cannot be always readily connected to the flocculation and the deposition of heavy fractions, and they are not always sensitive to the deposition of a small amount of such fractions. Some methods, such as the measurement of the absorbance in the infrared, are very sensitive, but difficult to implement under reservoir conditions.

Furthermore, since these methods are often used in the laboratory, the question which must also be considered concerns the representativeness of the samples on which the physical quantity measurements are performed. In fact, for a sample to be representative of the sampled fluid, it is necessary to maintain this sample under the pressure and temperature conditions that prevail for the sampled fluid, for example a reservoir fluid, throughout the sampling, sample transport and storage operations that are carried out prior to measurement.

The invention provides a method for determining the threshold of deposition of heavy fractions, notably asphaltenes, contained in the dissolved and/or stable colloidal state in a liquid hydrocarbon-containing fluid, based on the creation of an increasingly great pressure drop linked with the flow, at increasing flow rate, of a sample of said fluid through a capillary passage. Such a method has an improved selectivity and sensitivity in relation to the aforementioned prior methods and it allows to overcome the drawbacks of these methods. Furthermore, the method according to the invention can be implemented in situ in wells producing fluids, notably asphaltenic fluids, which also provides an answer to the problem of the representativeness of the samples measured.

SUMMARY OF THE INVENTION

The method according to the invention for determining the threshold of deposition of heavy fractions contained in the dissolved and/or stable colloidal state in a liquid, hydrocarbon-containing fluid is characterized in that it consists in:

bringing a sample of said fluid, maintained at a constant pressure and temperature such that the heavy fractions present in said fluid sample are in the dissolved and/or stable colloidal state, to the inlet of a capillary passage comprising an inlet and an outlet, and likely to generate a pressure drop between the inlet and the outlet that is at least equal to the difference between the pressure of the fluid sample and the bubble-point pressure of said sample, establishing an initial fluid pressure at the outlet of the capillary passage that is substantially equal to the pressure of the fluid sample brought to the inlet of said passage, generating, by operating at a constant temperature substantially equal to the temperature of the fluid sample, a flow of the liquid fluid, at an increasing flow rate, through the capillary passage, until the pressure at the outlet of the capillary passage has dropped from the original pressure to a predetermined pressure above the bubble-point pressure of the sample, measuring a difference $\Delta P$ between the pressure of the fluid at the inlet of the capillary passage and pressure Ps of the fluid at the outlet of said capillary passage and/or said outlet pressure Ps, as well as a quantity D representative of the flow of liquid flowing through the capillary passage, detecting a significant shift in the variation of one of quantities $\Delta P$ and D as a function of time or as a function of the other quantity or of a quantity representative of this other quantity, and defining as the deposition pressure of the heavy fractions at the operating temperature, for the liquid hydrocarbon-containing fluid subjected to the test, the fluid pressure at the outlet of the capillary passage which corresponds to a start of said shift, this pressure characterizing the threshold of deposition of the heavy fractions for said fluid.

In particular, the last two aforementioned stages of the method according to the invention can be carried out by representing, in form of a curve, the variation of one of the quantities ΔP and D as a function of time or as a function of the other quantity or of a quantity representative of this other quantity, and by defining as the deposition pressure of the heavy fractions at the operating temperature, for the liquid hydrocarbon-containing fluid subjected to the test, the fluid pressure at the outlet of the capillary passage which corresponds to the start of a change in the slope of the variation curve of quantity ΔP or of quantity D.

According to an embodiment, the capillary passage is filled with a stationary phase that can be selected, for example, from among the stationary phases used in high-pressure liquid chromatography.

Whether filled with a stationary phase or free from such a phase, the capillary passage has a void space advantageously ranging between 1 µl and 5000 µl, and more particularly between 10 µl and 100 µl.

The pressure of the liquid sample brought to the inlet of the capillary passage can vary quite widely and it can notably range between 5 bars and 1500 bars.

The volume of liquid sample sweeping the capillary passage during operation advantageously represents 50 to 500,000, preferably 10,000 to 100,000 times the void space of the capillary passage.

In a first embodiment of the method according to the invention, the liquid flow is generated at an increasing flow rate through the capillary passage by decreasing pressure Ps at the outlet of the capillary passage, continuously or in stages, according to a predetermined profile as a function of time, so as to change from the initial outlet pressure to the predetermined pressure above the bubble-point pressure of the sample, and the variation of quantity D is recorded, which is representative of the flow of liquid flowing through the capillary passage, as a function of time, when pressure Ps decreases in stages, or as a function of ΔP or of Ps, when pressure Ps decreases continuously, so as to produce the curve from which the deposition pressure of the heavy fractions is defined.

The pressure decrease at the outlet of the capillary passage can be generated in particular at a rate ranging between 0.1 and 50 bar/minute, and more particularly between 0.5 and 10 bar/minute.

In a second embodiment of the method according to the invention, the liquid flow is generated at an increasing flow rate through the capillary passage by discharging the liquid at the outlet of said capillary passage, with an increasing flow rate, continuously. or in stages, according to a predetermined law as a function of time, so as to change from the initial outlet pressure to the predetermined pressure above the bubble-point pressure of the sample, and the variation of quantity ΔP is recorded, which is representative of the difference between the fluid pressure at the inlet of the capillary passage and pressure Ps of the fluid at the outlet of said capillary passage, as a function of time, when the flow of liquid discharged increases in stages, or as a function of quantity D when said flow rate increases continuously, so as to produce the curve from which the deposition pressure of the heavy fractions is defined.

On the curves used to define the deposition pressure of the heavy fractions, it is also possible to measure the rate of variation of the slope of the portion of said curves starting at the point that corresponds to the deposition pressure of the heavy fractions, and said rate gives an indication of the rate of deposition of said heavy fractions.

The method according to the invention can also be used to evaluate the efficiency of an additive intended to inhibit or to retard the deposition of heavy fractions contained in a liquid hydrocarbon-containing fluid extracted from a reservoir. Determined amounts of additive are therefore injected into the hydrocarbon-containing fluid to be studied prior to introducing said fluid into the capillary passage, by operating under pressure and temperature conditions representative of the reservoir conditions, and the method is then implemented as mentioned above so as to produce the curves used for defining the deposition pressure of the heavy fractions. The efficiency of the additive can then be evaluated at two levels, (i) at the level of the displacement of the point of the curves corresponding to the deposition pressure of the heavy fractions and (ii) at the level of the rate of deposition measured by means of the rate of variation of the slope of the curve portion starting at said point corresponding to the deposition pressure of said heavy fractions.

According to a particular embodiment, the method according to the invention is implemented within the liquid hydrocarbon-containing fluid comprising heavy fractions, notably asphaltenes, in the dissolved and/or stable colloidal state, the inlet of the capillary passage being then directly in contact with said fluid.

A device for implementing the method according to the invention is characterized in that it comprises:

an inlet chamber for a liquid, equipped with delivery means and means for maintaining said liquid at a constant pressure in said chamber, an outlet chamber equipped with means providing generation of a flow of liquid at an increasing flow rate, and allowing to apply to said flow a rate or a pressure that varies continuously or in stages, and provided with means for measuring the pressure of the liquid in this chamber and a quantity D representative of the rate of the flowing liquid, a capillary line provided with an inlet and an outlet, and connected by its inlet to the inlet chamber and, by its outlet, to the outlet chamber, said capillary line being able to generate a pressure drop between its inlet and its outlet that is at least equal to the difference between the pressure of the liquid in the inlet chamber and the bubble-point pressure of this liquid.

The device according to the invention can also comprise means for maintaining the elements at constant temperature.

The capillary line can be filled with a stationary phase that can be selected as mentioned above for the capillary passage.

Whether filled with a stationary phase or free from such a phase, the capillary line has a void space that advantageously ranges between 1 µl and 5000 µl, more particularly between 10 µl and 100 µl.

The means for maintaining the liquid at a constant pressure in the inlet chamber can consist, for example, of a piston pump operated at said constant pressure.

According to a particular embodiment, which is especially interesting for implementing the method within the liquid hydrocarbon-containing fluid, the inlet chamber of the device has an open end opposite the inlet of the capillary line, which serves as delivery means and means for maintaining the liquid contained in said chamber at a constant pressure, when this chamber is immersed in the liquid hydrocarbon-containing fluid. With this embodiment, a filter is advantageously interposed between the open end of the inlet chamber and the inlet of the capillary line to prevent solid particles from being carried along.

The means that the outlet chamber is equipped with and which provide generation of a flow of liquid at increasing flow rate, continuously or in stages, can consist of (i) liquid draw-off means with a controlled downstream flow rate that increases continuously or in stages, for example a controlled and continuously or stepwise increasing downstream flow rate pump, or of (ii) draw-off means with a controlled and continuously or stepwise decreasing downstream pressure, for example, a throttling valve or a controlled and continuously or stepwise decreasing pressure pump.

In particular, the outlet chamber equipped with draw-off means for a liquid having a continuously or stepwise increasing flow rate consists of a cylindrical chamber in which a piston slides and moves in translation either under the action of a driving system intended to work at a speed that increases continuously or in stages, or by application of a pressure that decreases continuously or in stages. Said chamber is equipped with a pressure detector and with means for measuring the rate of displacement of the piston, said rate being a function of the flow of liquid discharged and, for example, proportional to said flow rate.

According to another embodiment, the outlet chamber and its equipments can also consist of the downstream portion of the capillary line, equipped with a pressure regulating valve, controlled by a variable control regulator, with a pressure detector connected to the regulator and with a flowmeter, arranged upstream from the valve, the inlet of said valve representing the outlet of the capillary line.

The device can also comprise additional means associated with the pressure measuring means in the outlet chamber and with the means for measuring quantity D representative of the flow of liquid and arranged to detect a significant shift in the variation of one of quantities $\Delta P$ and D as a function of time or as a function of the other quantity or of a quantity representative of this other quantity, quantity $\Delta P$ representing the pressure difference between the pressures in the inlet and outlet chambers, i.e. the pressure difference between the inlet and the outlet of the capillary line.

In particular, said additional means associated with the pressure measuring means in the outlet chamber and with the means for measuring quantity D representative of the flow of liquid can be recording means producing records, as a function of time, of said pressure and quantity D representative of the flow rate and/or producing the variation curve of quantity $\Delta P$ as a function of said quantity D or as a function of time, or the variation curve of said quantity D as a function of time or as a function of $\Delta P$ or of pressure Ps in the outlet chamber.

The device according to the invention, for which the inlet chamber is provided with an open end opposite the inlet of the capillary line and possibly comprises a filter interposed between said open end and the inlet of the capillary line, can be advantageously included in a bottomhole sample taker that can be lowered into a well producing the hydrocarbon-containing fluid including heavy fractions, notably asphaltenes, in such a way that the open end of the inlet chamber is visible.

BRIEF DESCRIPTION OF THE DRAWINGS

Other features and advantages of the invention will be clear from reading the description hereafter of an embodiment given by way of non limitative example, with reference to the accompanying drawings wherein.

DETAILED DESCRIPTION

Figure 1:
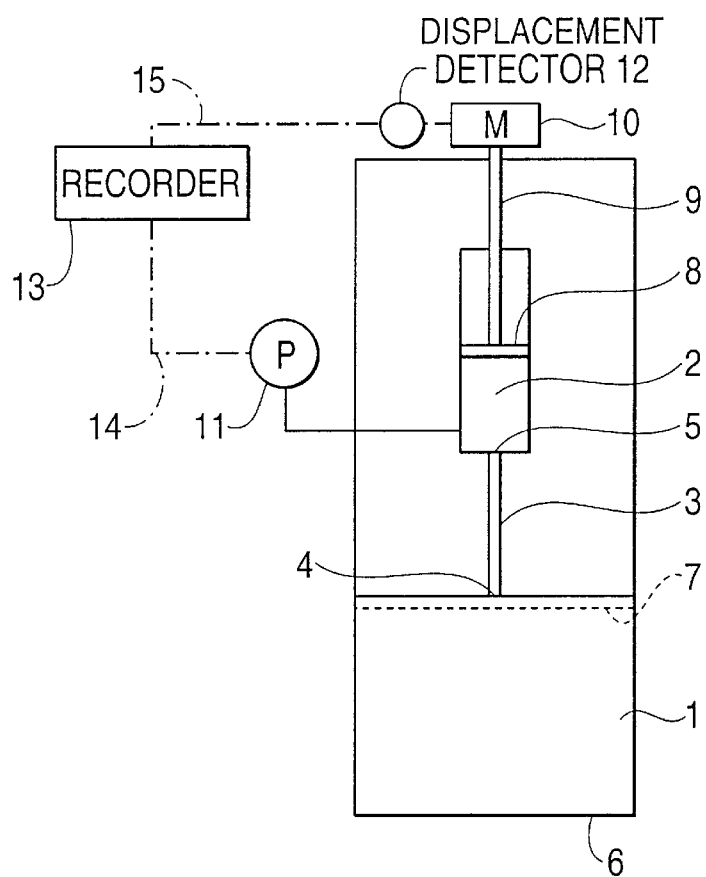
FIG. 1 is a diagrammatic view of a device for in-situ implementation of the method according to the invention.

The device shown in FIG. 1 comprises an inlet chamber 1 intended for a liquid, an outlet chamber 2 for a liquid and a capillary line 3, said capillary line comprising an inlet 4 and an outlet 5 and being connected, through the inlet thereof, to the inlet chamber, and through the outlet thereof, to the outlet chamber.

Inlet chamber 1, of cylindrical shape, has an open end opposite inlet 4 of the capillary line and it comprises a filter 7 interposed between said open inlet and inlet 4 of the capillary line.

Capillary line 3 is selected to be able to generate a pressure drop between the inlet and the outlet thereof that is at least equal to the difference between the pressure of the liquid in the inlet chamber and the bubble-point pressure of this liquid. For example, if the initial pressure of the liquid hydrocarbon-containing fluid produced by a hydrocarbon reservoir is 450 bars and the bubble-point pressure of said fluid is 200 bars, the capillary line is selected to be able to generate a pressure drop between the inlet and the outlet thereof that is at least 250 bars. Capillary line 3 can be filled with a stationary phase or it can be free from such a phase. In either case, the void space in the capillary line ranges between 1 $\mu$l and 5000 $\mu$l, more particularly between 10 $\mu$l and 100 $\mu$l.

Outlet chamber 2 is provided for drawing off liquid and it consists of a cylindrical chamber in which a piston 8 slides, which is extended by a rod 9 associated with a driving system 10 comprising a motor and allowing to drive in translation the piston at a continuously or stepwise increasing rate. Chamber 2 is equipped with a pressure detector 11 and the system for driving the piston in translation is associated with a detector 12 for measuring the rate of displacement of the piston, said rate being a function of the flow of liquid drawn off and, for example, proportional to this flow rate.

The device is associated with a recording system 13 to which are connected, at the respective outlets 14 and 15 thereof, pressure detector 11 and piston displacement rate detector 12, said recording system producing records, as a function of time, of said pressure, and rate, and/or a diagram of the variation of pressure difference $\Delta P$ between the pressures in the inlet and outlet chambers, i.e. the pressure difference between the inlet and the outlet of the capillary line, as a function of said rate V or as a function of time.

The device that has been described is used as mentioned hereafter for in-situ determination of the deposition threshold of heavy fractions, notably asphaltenes, contained, in the dissolved and/or colloidal state, in a liquid hydrocarbon-containing fluid under high pressure produced by a well drilled in a hydrocarbon reservoir.

The device included in a bottomhole sample taker so that open end 6 of inlet chamber 1 is visible is therefore lowered into the well producing the hydrocarbon-containing fluid comprising heavy fractions, notably asphaltenes.

Prior to lowering the device into the well, capillary line 3 and outlet chamber 2 are filled with a heavy fractions solvent notably intended for asphaltenes.

When the sample taker carrying the device according to the invention is set in the well, inlet chamber 1 of the device is filled, through open end 6, with the hydrocarbons-containing fluid to be studied. Filter 7 present in inlet chamber 1 retains the particles possibly carried along by the fluid, which might clog the capillary line. The fluid present in inlet chamber 1 is, throughout the measurement, at a constant pressure and temperature which are those prevailing in the well that contains the hydrocarbon-containing fluid to be studied and for which the heavy fractions, notably asphaltenes, contained in said fluid are in the dissolved and/or stable colloidal state. The temperature of the device remains also constant and equal to said temperature of the fluid at the well bottom.

The pressure in outlet chamber 2 is then adjusted, by displacing piston 8, to a value equal to that of the pressure of the fluid filling inlet chamber 1.

Figure 2A:
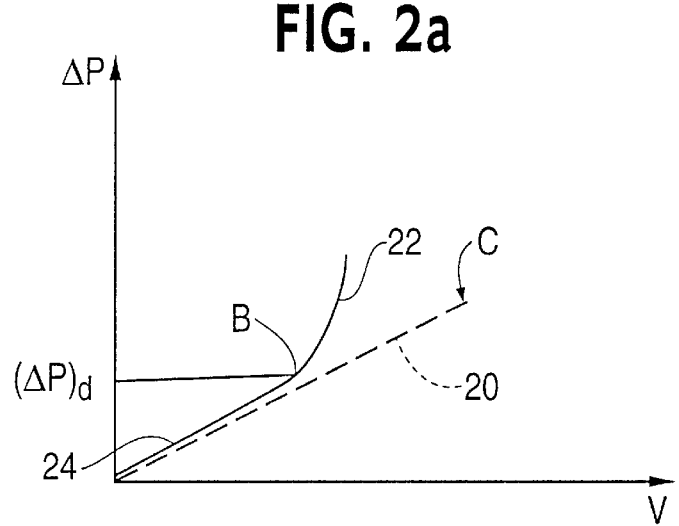
FIG. 2a is a diagram showing the variation of pressure difference $\Delta P$ as a function of a quantity representative of the flow of liquid drawn off.

By means of driving system 10, piston 8, whose position determines the volume of chamber 2, is then moved at a low increasing rate corresponding, for example, to a flow rate of 0.01 to 10 ml/minute, so as to increase the volume of outlet chamber 2 in order to create a continuous fluid flow in capillary line 3. The displacement of the piston leads to a progressive drop in the pressure of the liquid in outlet chamber 2, i.e. at the outlet of capillary line 3. The pressure in chamber 2 is measured by means of pressure detector 11, and the rate V of displacement of piston 8 is measured by means of detector 12, said rate being a function of the flow of fluid flowing through the capillary line and, for example, proportional to this flow rate. Signals 14 and 15 respectively delivered by pressure detector 11 and displacement rate detector 12 are recorded in a recording system 13 which establishes, among other things, a curve such as that shown in FIG. 2*a* and representing the variation of difference $\Delta P$ between the pressures of the fluid respectively at inlet 4 and at outlet 5 of the capillary line as a function of the rate of displacement V of the piston which is, in this case, proportional to the flow of liquid drawn off through capillary line 3. As shown in FIG. 2*a*, the pressure at the outlet of capillary line 3, i.e. the pressure in outlet chamber 2, has been reduced from the original value, equal to the pressure of the fluid prevailing in inlet chamber 1, to the bubble-point pressure of said fluid.

If the fluid flowing through the capillary line contained no heavy fractions, notably asphaltenes, no deposit would form in said line and the pressure difference $\Delta P$ would increase regularly with the flow of liquid drawn off, i.e. with the rate of displacement of the piston. The curve representative of the variation of the pressure difference $\Delta P$ as a function of rate V would have the regular course of dotted curve 20 in FIG. 2*a*, where point C gives the position of the bubble point.

On the other hand, when the fluid entering the capillary line contains heavy fractions, notably asphaltenes, in the dissolved and/or stable colloidal state, the pressure drop at the outlet of the capillary line leads to a solubility decrease of the heavy fractions, notably asphaltenes, in the fluid flowing through the capillary line. When the saturation threshold is reached, the heavy fractions, notably asphaltenes, flocculate and settle on the inner wall of the capillary line and also on the stationary phase, when there is one, and they clog said line. As a result of clogging of the capillary line by the heavy fractions, notably asphaltenes, quantity $\Delta P$ no longer follows the same variation law as a function of rate V as before clogging and it increases much faster. This leads to a change in the slope at point B, on the curve of FIG. 2*a* showing the variation of pressure difference $\Delta P$ as a function of rate V, between part 21 of said curve corresponding to the situation before clogging of capillary line 3 and part 22 of this curve corresponding to the situation after clogging.

Pressure $P_d$ determined from value $(\Delta P)_d$ at point B (deposition point) of the curve by relation $P_d = P_e - (\Delta P)_d$, where $P_e$ represents the pressure of the liquid in inlet chamber 1, defines the deposition pressure of the heavy fractions, notably asphaltenes, at the operating temperature for the fluid studied, said pressure characterizing the deposition threshold of the heavy fractions, notably asphaltenes, contained in said fluid.

It is also possible to increase the flow of liquid drawn off through the capillary line in stages. In the absence of clogging of the capillary line resulting from the deposition of heavy fractions, pressure difference $\Delta P$ takes on a substantially constant value at each flow rate stage. On the other hand, when the heavy fractions, notably asphaltenes, start to settle, an instability of the pressure difference $\Delta P$ is observed, i.e. an increase in this difference with time for a given flow rate stage. This behaviour can be observed by recording the pressure difference $\Delta P$ as a function of time. On the record obtained, which shows the course of a stepped curve similar to that shown in FIG. 3*a*, it is also possible to define a value $(\Delta P)_d$ at point D of the stepped curve which corresponds to the beginning of the first pressure instability plateau 25*i*. This value $(\Delta P)_d$ allows, as mentioned above, to define the deposition pressure $P_d$ of the heavy fractions, notably asphaltenes, at the operating temperature for the fluid studied, which characterizes the deposition threshold of the heavy fractions, notably asphaltenes, contained in said fluid.

Figure 4:
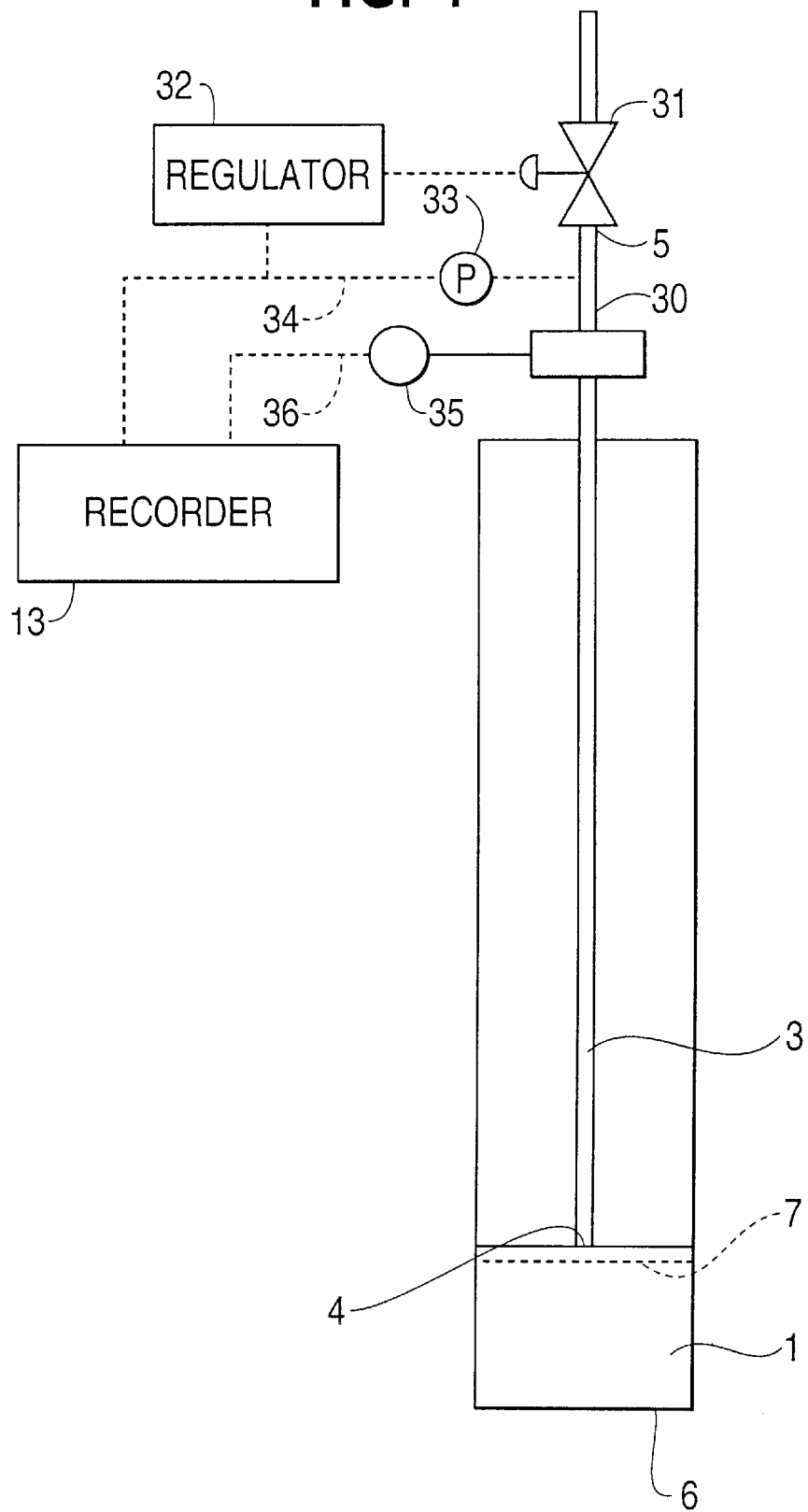

In a variant, a device similar to the device shown in FIG. 4 was used, which differs from the device shown in FIG. 1 in that outlet chamber 2 and its equipments consist of the downstream portion 30 of capillary line 3, equipped with a pressure regulating valve 31, controlled by a variable control regulator 32, with a pressure detector 33 connected by an outlet 34 to the regulator and to recorder 13, and with a flowmeter 35 arranged upstream from valve 31 and connected by an outlet 36 to said recorder. The inlet of valve 31 represents outlet 5 of the capillary line.

The device of FIG. 4 works in the same way as the device of FIG. 1. Pressure $P_s$ in downstream portion 30 of capillary line 3, which serves as the outlet chamber, is initially adjusted to a value slightly below the pressure value of the fluid filling inlet chamber 1. Actuation of valve 31 progressively decreases pressure $P_s$ of the fluid so as to create a flow with an increasing flow rate in capillary line 3. The pressure and the flow rate of the liquid are measured in portion 30 of capillary line 3, at the inlet of valve 31, by means of pressure detector 33 and of flowmeter 35, respectively. Signals 34 and 36 respectively delivered by pressure detector 33 and flowmeter 35 are recorded in recording system 13; this system establishes, among other things, a curve, such as that shown in FIG. 2*b*, which represents the variation of flow rate D of the liquid flowing through capillary line 3, as a function of the difference $\Delta P$ between the pressures of the fluid respectively at inlet 4 and at outlet 5 of the capillary line. An equivalent curve could also be formed by representing the variation of flow rate D of the liquid flowing through capillary line 3 as a function of pressure $P_s$ of the fluid at outlet 5 of the capillary line.

If the fluid flowing through the capillary line contained no heavy fractions, notably asphaltenes, no deposit would form in said line and the flow of liquid flowing through said line would increase regularly with the pressure difference ΔP. The curve representative of the variation of the flow of liquid flowing through capillary line 3 as a function of the pressure difference ΔP would have the regular course of dotted curve 40 in FIG. 2b, where point C gives the position of the bubble point.

Figure 2B:
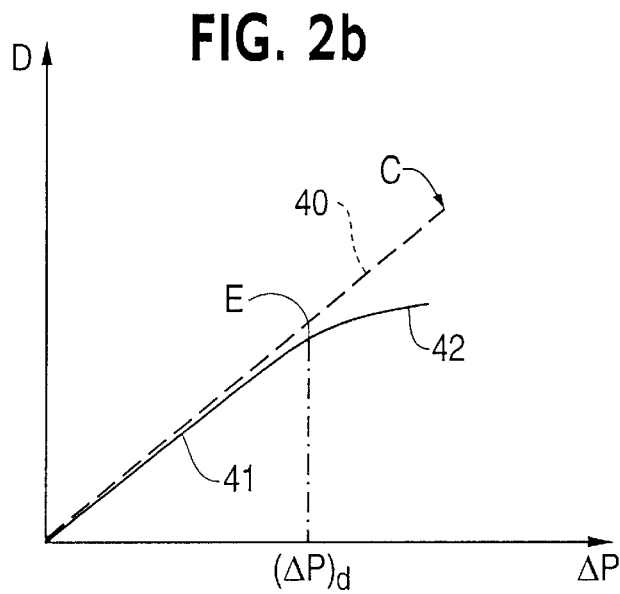
FIG. 2b is a diagram showing the variation of the flow of liquid drawn off as a function of pressure Ps in the outlet chamber.

On the other hand, when the fluid entering the capillary line contains heavy fractions, notably asphaltenes, in the dissolved and/or stable colloidal state, the pressure drop at the outlet of the capillary line leads to a decrease in the solubility of the heavy fractions, notably asphaltenes, in the fluid flowing through the capillary line. When the saturation threshold is reached, the heavy fractions, notably asphaltenes, flocculate and settle on the inner wall of the capillary line and also on the stationary phase, if there is one, and they clog said line. As a result of clogging of the capillary line by the heavy fractions, notably asphaltenes, the flow of liquid flowing through this line no longer follows the same variation law as a function of quantity ΔP as before clogging and it increases less rapidly. This leads, on the curve of FIG. 2b representing the variation of flow rate D of the liquid flowing through capillary line 3, as a function of the pressure difference ΔP, to a change in the slope at point E between part 41 of said curve corresponding to the situation before clogging of capillary line 3 and part 42 of this curve corresponding to the situation after clogging.

Pressure $P_d$ determined from value $(\Delta P)_d$ at point E (deposition point) of the curve by relation $P_d = P_e - (\Delta P)_d$, where $P_e$ represents the pressure of the liquid in inlets chamber 1, defines the deposition pressure of the heavy fractions, notably asphaltenes, at the operating temperature for the fluid studied, said pressure characterizing the deposition threshold of the heavy fractions, notably asphaltenes, contained in said fluid.

It is also possible to increase the difference ΔP between the pressures of the fluid respectively at inlet 4 and at outlet 5 of the capillary line in stages. In the absence of clogging of the capillary line due to the deposition of heavy fractions, the flow of liquid drawn off through capillary line 3 takes on a substantially constant value at each ΔP increase stage. On the other hand, when the heavy fractions, notably asphaltenes, start to settle, an instability of the flow rate is observed, i.e. a decrease in said flow rate with time for a given ΔP stage. This behaviour can be observed by recording the flow rate D of the liquid drawn off through capillary line 3 as a function of time. On the record obtained, which shows the course of a stepped curve similar to that shown in FIG. 3b, it is also possible to define a value $(\Delta P)_d$ at point F of the stepped curve which corresponds to the beginning of the first flow rate instability plateau 45i. This value $(\Delta P)_d$ allows, as mentioned above, to define deposition pressure $P_d$ of the heavy fractions, notably asphaltenes, at the operating pressure for the fluid studied, which characterizes the deposition threshold of the heavy fractions, notably asphaltenes, contained in said fluid.

It is also possible to obtain an indication of the rate of deposition of the heavy fractions from the curves used to define the deposition pressure of said heavy fractions.

As can be seen for example on the curve of FIG. 2a or the curve of FIG. 2b, the curve portion starting at the point corresponding to the deposition pressure of the heavy fractions, for example portion 22 in FIG. 2a or portion 42 in FIG. 2b, has a slope that increases (portion 22) or decreases (portion 42) as clogging of capillary line 3 by the heavy fractions that settle therein increases. The rate of variation of the slope of the curve portion starting at the point corresponding to the deposition pressure of the heavy fractions, for example the rate of increase of the slope of portion 22 in FIG. 2a or the rate of decrease of the slope of portion 42 in FIG. 2b, consequently gives an indication of the rate of deposition of the heavy fractions in capillary line 3, deposition being all the faster as said rate of variation is high.

Figure 5:
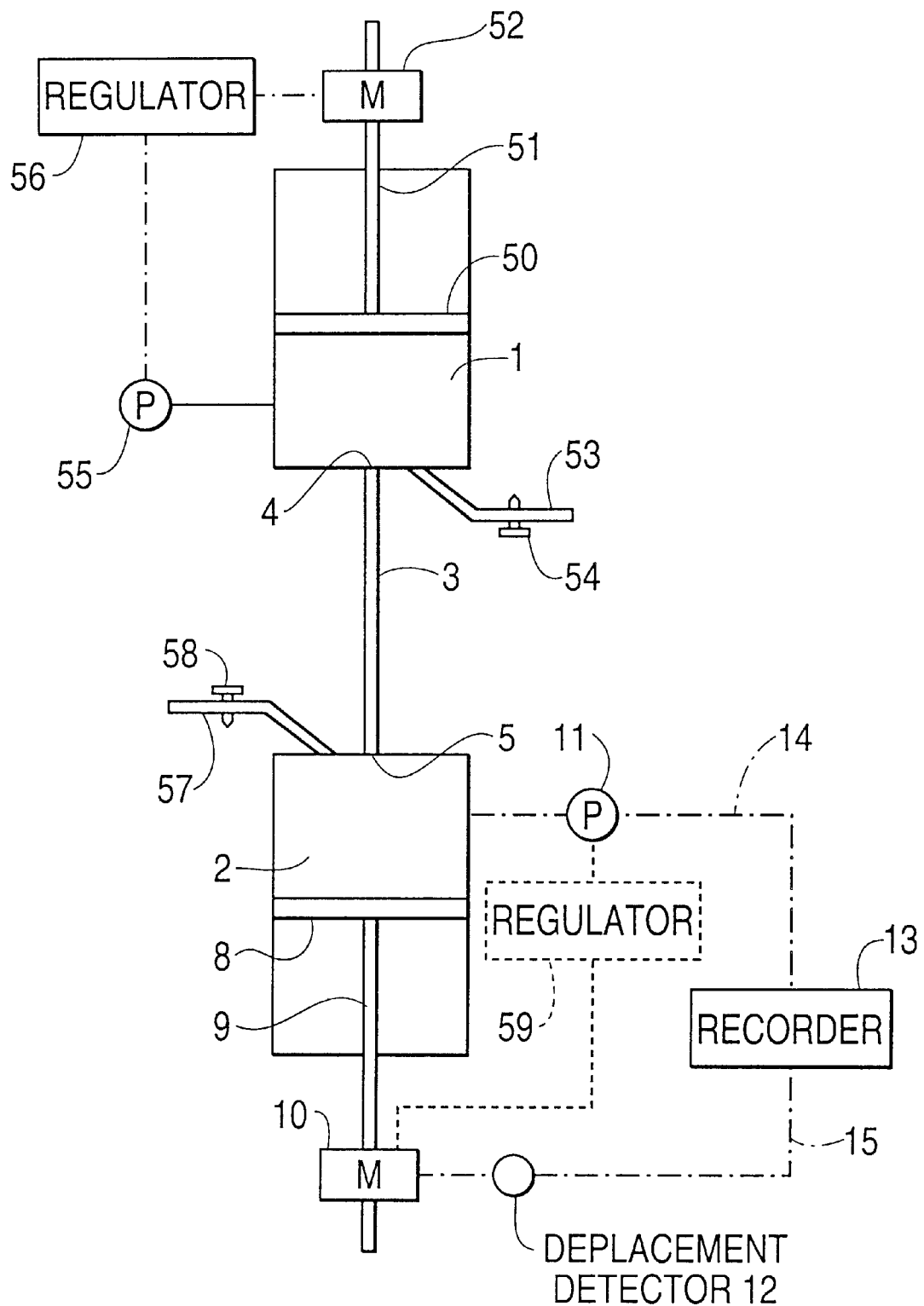
FIG. 5 is a diagrammatic view of a device intended for implementation of the method according to the invention in the laboratory.

The device shown in FIG. 5 comprises an inlet chamber 1 intended for a liquid, an outlet chamber 2 for a liquid, and a capillary line 3, said capillary line having an inlet 4 and an outlet 5, and being connected, by the inlet thereof to the inlet chamber, and by the outlet thereof, to the outlet chamber.

Inlet chamber 1 consists of a cylindrical chamber in which slides a piston 50 extended by a rod 51 associated with a driving system 52 comprising a motor and allowing the piston to be driven in translation. Chamber 1 is also equipped with a line 53 provided with a shutting valve 54, intended for delivery of the fluid to be studied, and with a pressure detector 55. A regulator 56 connected to system 52 intended to drive the piston in translation and receiving information from pressure detector 55 controls the rate of displacement of the piston so as to maintain the pressure of the fluid in chamber 1 at a predetermined value.

Capillary line 3 is selected, as mentioned above, to generate a pressure drop between the inlet and the outlet thereof that is at least equal to the difference between the pressure of the liquid in the inlet chamber and the bubble-point pressure of this liquid. Capillary line 3 can be filled with a stationary phase or free from such a phase and, in either case, its void space has the same value as that mentioned above.

Outlet chamber 2 consists of a cylindrical chamber in which slides a piston 8 extended by a rod 9 associated with a driving system 10 comprising a motor and intended to drive the piston in translation at an imposed rate that increases continuously or in stages, which corresponds to a fluid discharge out of capillary line 3 with an imposed flow rate that increases continuously or in stages. Chamber 2 is equipped with a pressure detector 11 and the system intended to drive the piston in translation is associated with a detector 12 for measuring the rate of displacement of the piston, said rate being a function of the flow of liquid drawn off, and for example proportional to this flow rate.

Chamber 2 is also provided with a line 57 provided with a shutting valve 58, for delivery of the liquid in said chamber.

In a variant, the piston is driven no longer to discharge liquid out of the capillary line at an imposed rate, but to discharge liquid out of the capillary line at an imposed pressure that decreases continuously or in stages. A regulator 59 connected to system 10 driving piston 8 in translation and receiving information from pressure detector 11 therefore controls for example the displacement of the piston so as to decrease the pressure of the fluid in chamber 2 according to the predetermined profile.

The device is associated with a recording system 13 to which are connected, through the respective outlets 14 and 15 thereof, pressure detector 11 and detector 12 measuring the rate of displacement of the piston or the flow rate, and said recording system produces records, as a function of time, of said pressure and rate of displacement or flow rate and/or it produces a diagram of the variation of the pressure difference ΔP between the pressures in the inlet and outlet chambers, i.e. the pressure difference between the inlet and the outlet of the capillary line, as a function of time or of said rate, or a diagram of the variation in the flow of liquid drawn off as a function of time or of quantity ΔP.

The device that has been described can be used as mentioned above for determination in the laboratory of the deposition threshold of the heavy fractions, notably asphaltenes, contained in the dissolved and/or colloidal state, in a liquid hydrocarbon-containing fluid under high pressure produced by a well drilled in a hydrocarbon reservoir.

Capillary line 3 and outlet chamber 2 are therefore filled with a heavy fractions solvent notably intended for asphaltenes, introduced through line 57 in chamber 2.

A sample of the hydrocarbon-containlng fluid comprising heavy fractions, notably asphaltenes, is introduced through line 53 into inlet chamber 1 and the pressure of the fluid in said chamber is adjusted to the desired value, for example equal to the pressure prevailing in the well comprising the hydrocarbon-containing fluid to be studied.

The device is placed in a thermostat-controlled enclosure that is not shown in FIG. 5 and which maintains it at the selected temperature, for example the temperature of the fluid at the well bottom.

The pressure in outlet chamber 2 is then adjusted, by displacement of piston 8, to a value equal to that of the pressure of the fluid filling inlet chamber 1.

By means of driving system 10, piston 8, whose position determines the volume of chamber 2, is then moved so as to increase the volume of outlet chamber 2 in order to create a continuous fluid flow in capillary line 3. The displacement of the piston is controlled to provide discharge of the liquid out of the capillary line, either at a flow rate that increases continuously or in stages, according to an imposed profile, or at a pressure that decreases continuously or in stages, according to an imposed profile.

The displacement of the piston leads to a progressive drop in the pressure of the liquid in outlet chamber 2, i.e. at the outlet of capillary line 3. The pressure in chamber 2 is measured by means of pressure detector 11, and the rate of displacement of piston 8 is measured by means of detector 12, said rate of displacement being a function of the flow of fluid flowing through the capillary line and, for example, proportional to this flow rate. Signals 14 and 15 respectively delivered by pressure detector 11 and displacement rate detector 12 are recorded in a recording system 13; said system establishes, among other things, curves comparable to those shown in FIGS. 2a, 2b, 3a, and 3b described above.

The device of FIG. 5 can be advantageously used to evaluate the efficiency of an additive intended to inhibit or to retard the formation of deposits of heavy fractions contained in a liquid hydrocarbon-contaig fluid extracted from a reservoir. Determined amounts of additive are therefore injected, under pressure and temperature conditions representative of those prevailing in the reservoir, into a sample of the hydrocarbon-containing fluid to be studied prior to introducing said sample into inlet chamber 1 of the device, and the method according to the invention is implemented in said device as described above, so as to produce the curves used to define the deposition pressure of the heavy fractions. The efficiency of the additive can then be evaluated at two levels: (i) at the level of the displacement of the point of the curves corresponding to the deposition pressure of the heavy fractions, and (ii) at the level of the rate of deposition measured by means of the rate of variation of the slope of the curve portion beginning at said point corresponding to the deposition pressure of the heavy fractions.

Figure 3A:
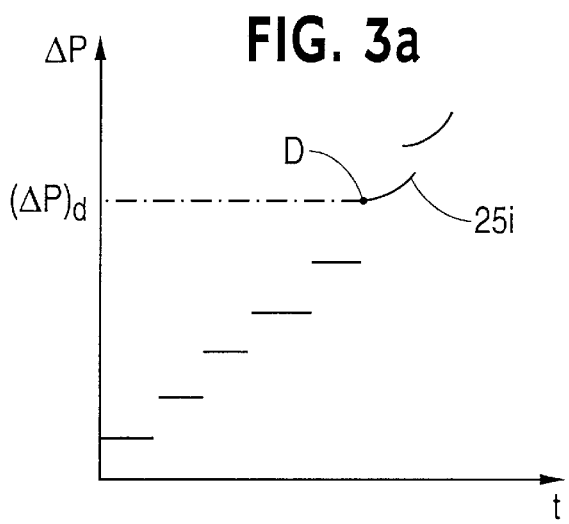
FIG. 3a is a diagram showing the variation of pressure difference $\Delta P$ as a function of time for a stepwise variation of the flow of liquid drawn off.
Figure 3B:
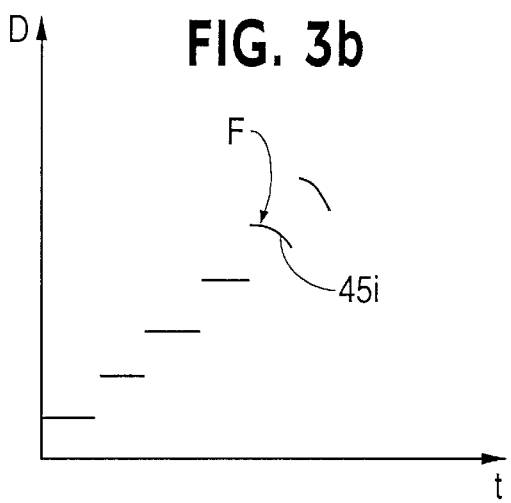
FIG. 3b is a diagram showing the variation of the flow of liquid drawn off as a function of time, for a stepwise variation of pressure difference $\Delta P$, FIG. 4 diagrammatically shows a variant of the device of FIG. 1.

Thus, when the presence of an additive in the fluid studied leads to a displacement of points B in FIG. 2a, E in FIG. 2b, D in FIG. 3a, and F in FIG. 3b towards higher ΔP values, this means that this additive has a favourable effect on the widening of the pressure range within which the heavy fractions remain in the dissolved and/or stable colloidal state in said fluid.

Furthermore, the decrease in the rate of variation of the slope of the curve portion beginning at the point corresponding to the deposition pressure of the heavy fractions, for example the rate of increase of the slope of portion 22 in FIG. 2a or the rate of decrease of the slope of portion 42 in FIG. 2b, also shows the favourable effect of the additive intended to inhibit or retard the formation of deposits of heavy fractions contained in the fluid.

What is claimed is:

1. A method for determining the deposition threshold of heavy fractions contained in the dissolved and/or stable colloidal state in a liquid hydrocarbon-containing fluid, comprising the following steps:
   (a) driving a sample of the fluid, maintained at a constant pressure and temperature and such that the heavy fractions present in the fluid sample are in the dissolved and/or stable colloidal state, to an inlet of a capillary line to generate a pressure drop between an inlet pressure and an outlet pressure respectively between an inlet and an outlet of the capillary line at least equal to a difference between the pressure of the fluid sample and a bubble-point pressure of the fluid sample;
   (b) establishing an initial outlet pressure equal to the inlet pressure;
   (c) generating, by operating at a constant temperature equal to the temperature of the fluid sample, a flow of the liquid hydrocarbon-containing fluid, at an increasing flow rate, through the capillary line, until the outlet pressure has dropped from the initial pressure to a predetermined pressure above the bubble-point pressure of the fluid sample;
   (d) measuring a pressure difference ΔP between the inlet pressure and the outlet pressure (Ps) and/or the outlet pressure (Ps) as well as a flow rate (D) of the liquid hydrocarbon-containing fluid flowing through the capillary line;
   (e) detecting a change in the variation rate of a first of the two quantities pressure difference (ΔP) and flow rate (D) as a function of time, or as a function of the second of the two quantities, or of a quantity representative of the second of the two quantities; and
   (f) defining as a deposition pressure of the heavy fractions, at the constant temperature, for the liquid hydrocarbon-containing fluid, the fluid pressure at the outlet of the capillary line which corresponds to a start of the change in variation rate, this pressure characterizing the deposition threshold of the heavy fractions for the fluid sample.

2. A method as claimed in claim 1, wherein the capillary line is filled with a stationary phase.

3. A method as claimed in claim 1, wherein the capillary line has a void space ranging between 1 $\mu l$ and 5000 $\mu l$, and more particularly between 10 $\mu l$ and 100 $\mu l$.

4. A method as claimed in claim 1, wherein the pressure of the fluid sample driven to the inlet of the capillary line ranges between 5 bars and 1500 bars.

5. A method as claimed in claim 1, wherein the volume of fluid sample sweeping the capillary line for determining the deposition threshold represents 50 to 500000 times the void space of the capillary line.

6. A method as claimed in claim 1, wherein steps (e) and (f) are carried out by representing, in the form of a curve, the variation of a first of the two quantities pressure difference ($\Delta P$) and flow rate (D) as a function of time or as a function of the second of the two quantities or of a quantity representative of the second of the two quantities, and by defining as the deposition pressure of the heavy fractions, at the operating temperature, for the liquid hydrocarbon-containing fluid, the outlet pressure of the fluid which corresponds to the start of a change in the variation curve of the two quantities.

7. A method as claimed in claim 6, further comprising generating an increasing flow rate through the capillary line, by decreasing the outlet pressure Ps continuously or by stages, according to a predetermined profile as a function of time, recording variations of the flow rate as a function of time, when pressure Ps decreases by stages, or as a function of the pressure difference ($\Delta P$) or the outlet pressure (Ps) when the outlet pressure (Ps) decreases continuously, so as to produce the curve from which the deposition pressure of the heavy fractions is defined.

8. A method as claimed in claim 7, wherein the outlet pressure is decreased at a rate ranging between 0.1 and 50 bar/minute.

9. A method as claimed in claim 7, wherein the outlet pressure is decreased at a rate ranging between 0.5 and 10 bar/minute.

10. A method as claimed in claim 6, further comprising generating an increasing flow rate through the capillary line by discharging the fluid at the outlet of said capillary line, with a flow rate that increases continuously or by stages, according to a predetermined law as a function of time, and recording variations of the pressure difference ($\Delta P$) as a function of time when the flow of fluid discharged increases by stages, or as a function of flow rate (D) when the flow rate increases continuously, so as to produce the curve from which the deposition pressure of the heavy fractions is defined.

11. A method as claimed in claim 1, wherein the volume of fluid sample sweeping the capillary line for determining the deposition threshold represents 10000 to 100000 times the void space of the capillary line.

12. A device for determining the flocculation threshold of heavy fractions contained, in the dissolved and/or colloidal state, in a liquid hydrocarbon-containing fluid, comprising:

an inlet chamber for a liquid, provided with pressure regulating means delivering the fluid at a constant pressure in the inlet chamber;

a capillary line having an inlet connected to the inlet chamber, the capillary line generating a pressure drop between the inlet and an outlet thereof that is at least equal to a difference between the pressure of the fluid in the inlet chamber and a bubble-point pressure of the fluid; and an outlet chamber connected with the outlet of the capillary line and associated with flow regulating means for providing a liquid flow with a flow rate or a pressure that varies continuously or by stages, and provided with pressure measuring means for measuring the pressure of the fluid in the outlet chamber and for measuring a flow rate (D) of the liquid hydrocarbon-containing fluid flowing through the capillary line.

13. A device as claimed in claim 12, wherein the capillary line is filled with a stationary phase.

14. A device as claimed in claim 13, wherein the capillary line has a void space ranging between 1 $\mu$l and 5000 $\mu$l.

15. A device as claimed in claim 13, wherein the capillary line has a void space ranging between 10 $\mu$l and 100 $\mu$l.

16. A device as claimed in claim 12, wherein the flow regulating means include means for discharging fluid at a controlled downstream flow rate that increases continuously or by stages, or means for discharging fluid at a controlled downstream flow rate that decreases continuously or by stages.

17. A device as claimed in claim 16, wherein the outlet chamber includes a cylindrical chamber, a piston sliding in the cylindrical chamber, a driving system for moving the piston at a speed that increases continuously or by stages, or by application of a pressure that decreases continuously or by stages, the outlet chamber being provided with a pressure detector and with a measuring element for measuring a rate of displacement of the piston which is a function of the flow of fluid discharged.

18. A device as claimed in claim 16, wherein the outlet chamber includes a downstream portion of the capillary line provided with a pressure regulating valve, the device further comprising a variable control regulator for controlling the pressure regulating valve, a pressure detector connected to the variable control regulator and a flowmeter arranged upstream from the pressure regulating valve, the inlet of the pressure regulating valve representing the outlet of the capillary line.

19. A device as claimed in claim 12, further comprising recording means associated with a pressure sensor for measuring the pressure in the outlet chamber and with means for measuring a flow rate (D) and detecting a change in the variation rate of the two of quantities pressure difference between the respective pressures in the inlet chamber and the outlet chamber and flow rate (D) as a function of time, or as a function of the second of the two quantities, or of a quantity representative of the second of the two quantities.

20. A device as claimed in claim 19, wherein the recording means includes means producing records, as a function of time, of the respective pressures and flow rate, and means for producing a variation curve of the pressure difference as a function of the flow rate (D), or as a function of time, or a variation curve of the flow rate (D) as a function of time or as a function of the pressure difference or of pressure in the outlet chamber.

21. A device as claimed in claim 12, wherein inlet chamber is provided with an open end opposite the inlet of the capillary line, whereby the fluid contained in the inlet chamber is maintained at a constant pressure when the inlet chamber is immersed in the liquid hydrocarbon-containing fluid.

22. A device as claimed in claim 21, further comprising a filter interposed between the open end of inlet chamber and the inlet of capillary line.

23. A device as claimed in claim 21, further comprising a bottomhole sampler to be lowered into a well producing the hydrocarbon-containing fluid comprising heavy fractions, the open end of inlet chamber being opened to produce fluid.

* * * * *